US007651533B2

(12) United States Patent
Legrand

(10) Patent No.: US 7,651,533 B2
(45) Date of Patent: *Jan. 26, 2010

(54) DYE COMPOSITION WITH A REDUCED CONTENT OF STARTING MATERIALS, PROCESS FOR DYEING KERATIN FIBERS USING THE SAME AND DEVICE THEREFOR

(76) Inventor: Frédéric Legrand, 2-1-4 Ichigayasadoharacho, Crest court Sadohara #313, Shinjuku-ku, 162-0842 Tokyo (JP)

( * ) Notice: Subject to any disclaimer, the term of this patent is extended or adjusted under 35 U.S.C. 154(b) by 114 days.

This patent is subject to a terminal disclaimer.

(21) Appl. No.: 11/393,694

(22) Filed: Mar. 31, 2006

(65) Prior Publication Data

US 2006/0260068 A1    Nov. 23, 2006

Related U.S. Application Data

(60) Provisional application No. 60/681,171, filed on May 16, 2005.

(30) Foreign Application Priority Data

Mar. 31, 2005    (FR)    ................................... 05 50837

(51) Int. Cl.
    *A61Q 5/10*    (2006.01)
(52) U.S. Cl. ....................... 8/405; 8/406; 8/407; 8/435; 8/552; 8/554; 8/559; 8/580; 8/582
(58) Field of Classification Search .................... 8/405, 8/406, 407, 435, 552, 554, 559, 580, 582
    See application file for complete search history.

(56) References Cited

U.S. PATENT DOCUMENTS

| 2,261,002 A | 10/1941 | Ritter |
| 2,271,378 A | 1/1942 | Searle |
| 2,273,780 A | 2/1942 | Dittmar |
| 2,375,853 A | 5/1945 | Kirby et al. |
| 2,388,614 A | 11/1945 | Kirby et al. |
| 2,454,547 A | 11/1948 | Bock et al. |
| 2,961,347 A | 11/1960 | Floyd |
| 3,206,462 A | 9/1965 | McCarty |
| 3,227,615 A | 1/1966 | Korden |
| 3,472,840 A | 10/1969 | Stone et al. |
| 3,589,578 A | 6/1971 | Kamphausen |
| 3,632,559 A | 1/1972 | Matter et al. |
| 3,836,537 A | 9/1974 | Boerwinkle et al. |
| 3,874,870 A | 4/1975 | Green et al. |
| 3,910,862 A | 10/1975 | Barabas et al. |
| 3,912,808 A | 10/1975 | Sokol |
| 3,917,817 A | 11/1975 | Vanlerberghe et al. |
| 3,929,990 A | 12/1975 | Green et al. |
| 3,966,904 A | 6/1976 | Green et al. |
| 3,986,825 A | 10/1976 | Sokol |
| 4,001,432 A | 1/1977 | Green et al. |
| 4,005,193 A | 1/1977 | Green et al. |
| 4,013,787 A | 3/1977 | Varlerberghe et al. |
| 4,025,617 A | 5/1977 | Green et al. |
| 4,025,627 A | 5/1977 | Green et al. |
| 4,025,653 A | 5/1977 | Green et al. |
| 4,026,945 A | 5/1977 | Green et al. |
| 4,027,008 A | 5/1977 | Sokol |
| 4,027,020 A | 5/1977 | Green et al. |
| 4,031,307 A | 6/1977 | DeMartino et al. |
| 4,075,136 A | 2/1978 | Schaper |
| 4,116,894 A | 9/1978 | Lentz et al. |
| 4,131,576 A | 12/1978 | Iovine et al. |
| 4,157,388 A | 6/1979 | Christiansen |
| 4,165,367 A | 8/1979 | Chakrabarti |
| 4,166,894 A | 9/1979 | Schaper |
| 4,172,887 A | 10/1979 | Vanlerberghe et al. |
| 4,189,468 A | 2/1980 | Vanlerberghe et al. |
| 4,197,865 A | 4/1980 | Jacquet et al. |
| 4,217,914 A | 8/1980 | Jacquet et al. |
| 4,223,009 A | 9/1980 | Chakrabarti |
| 4,240,450 A | 12/1980 | Grollier et al. |
| 4,277,581 A | 7/1981 | Vanlerberghe et al. |

(Continued)

FOREIGN PATENT DOCUMENTS

| DE | 30 30 119 | 11/1987 |
| DE | 38 34 142 | 4/1990 |
| DE | 41 27 230 | 2/1993 |
| DE | 41 03 292 | 2/1994 |
| DE | 101 32 915 | 1/2003 |

(Continued)

OTHER PUBLICATIONS

French Search Report for French Patent Application No. FR 05/50837, priority document for co-pending U.S. Appl. No. 11/393,694, Nov. 10, 2005.
International Search report for European Patent Application No. EP06111861.8, European counterpart application for co-pending U.S. Application No. 11/393,694, Jun. 14, 2006.
English Language Derwent Abstract for DE 41 03 292. (Feb. 1994).
English Language Derwent Abstract for DE 38 34 142. (Apr. 1990).
English Language Derwent Abstract for DE 30 30 119. (Nov. 1987).
English Language Derwent Abstract for EP 1 518 547. (Mar. 2005).
English Language Derwent Abstract for EP 0 122 324. (Oct. 1984).
English Language Derwent Abstract for EP 1 048 289. (Nov. 2000).
English Language Derwent Abstract for FR 2 717 076. (Sep. 1995).

(Continued)

*Primary Examiner*—Eisa B Elhilo

(57) ABSTRACT

The present disclosure relates to a dye composition comprising at least one dye, at least one nonionic surfactant, at least one anionic surfactant, at least one fatty alcohol and at least one non-ethoxylated fatty acid ester; the weight ratio of the total amount of fatty alcohols to the total amount of nonionic and anionic surfactants being greater than 0.5 and the water content comprising at least 55% by weight. The disclosure similarly relates to a process for dyeing keratin fibers, for example human keratin fibers, using such a composition, and also to a multi-compartment device comprising the dye composition in the first compartment, and an oxidizing composition in the second compartment.

28 Claims, No Drawings

U.S. PATENT DOCUMENTS

| | | |
|---|---|---|
| 4,348,202 A | 9/1982 | Grollier et al. |
| 4,349,532 A | 9/1982 | Vanlerberghe et al. |
| 4,381,919 A | 5/1983 | Jacquet et al. |
| 4,422,853 A | 12/1983 | Jacquet et al. |
| 4,445,521 A | 5/1984 | Grollier et al. |
| 4,579,732 A | 4/1986 | Grollier et al. |
| 4,591,610 A | 5/1986 | Grollier |
| 4,608,250 A | 8/1986 | Jacquet et al. |
| 4,702,906 A | 10/1987 | Jacquet et al. |
| 4,719,099 A | 1/1988 | Grollier et al. |
| 4,719,282 A | 1/1988 | Nadolsky et al. |
| 4,761,273 A | 8/1988 | Grollier et al. |
| 4,777,040 A | 10/1988 | Grollier et al. |
| 4,803,221 A | 2/1989 | Bair |
| 4,839,166 A | 6/1989 | Grollier et al. |
| 4,919,923 A | 4/1990 | Hoeffkes et al. |
| 4,948,579 A | 8/1990 | Jacquet et al. |
| 4,970,066 A | 11/1990 | Grollier et al. |
| 4,996,059 A | 2/1991 | Grollier et al. |
| 5,009,880 A | 4/1991 | Grollier et al. |
| 5,057,311 A | 10/1991 | Kamegai et al. |
| 5,089,252 A | 2/1992 | Grollier et al. |
| 5,139,037 A | 8/1992 | Grollier et al. |
| 5,196,189 A | 3/1993 | Jacquet et al. |
| 5,480,459 A | 1/1996 | Mager et al. |
| 5,494,489 A | 2/1996 | Akram et al. |
| 5,708,151 A | 1/1998 | Möckli |
| 5,792,221 A | 8/1998 | Lagrange et al. |
| 5,958,392 A | 9/1999 | Grollier et al. |
| 5,990,233 A | 11/1999 | Barron et al. |
| 6,106,578 A | 8/2000 | Jones |
| 6,436,151 B2 * | 8/2002 | Cottard et al. ............... 8/406 |
| 6,540,791 B1 * | 4/2003 | Dias ........................... 8/111 |
| 6,613,315 B1 | 9/2003 | Dupuis |
| 6,800,098 B1 | 10/2004 | Allard et al. |
| 6,824,570 B2 | 11/2004 | Vidal et al. |
| 6,881,230 B2 | 4/2005 | Vidal |
| 6,884,265 B2 | 4/2005 | Vidal et al. |
| 6,884,267 B2 | 4/2005 | Vidal et al. |
| 6,893,471 B2 | 5/2005 | Vidal |
| 7,001,436 B2 | 2/2006 | Vidal et al. |
| 7,022,143 B2 | 4/2006 | Vidal et al. |
| 7,060,110 B2 | 6/2006 | Vidal et al. |
| 7,077,873 B2 | 7/2006 | David et al. |
| 7,261,743 B2 | 8/2007 | Plos et al. |
| 7,326,256 B2 | 2/2008 | Cottard et al. |
| 7,442,214 B2 * | 10/2008 | Legrand ...................... 8/405 |
| 2001/0023514 A1 | 9/2001 | Cottard et al. |
| 2002/0095732 A1 | 7/2002 | Kravtchenko et al. |
| 2003/0084516 A9 | 5/2003 | Kravtchenko et al. |
| 2003/0106169 A1 | 6/2003 | Vidal et al. |
| 2003/0124079 A1 | 7/2003 | Mougin et al. |
| 2003/0192134 A1 | 10/2003 | Desenne et al. |
| 2004/0047821 A1 | 3/2004 | Maubru et al. |
| 2004/0060126 A1 | 4/2004 | Cottard et al. |
| 2004/0093675 A1 | 5/2004 | Vidal et al. |
| 2004/0093676 A1 | 5/2004 | Vidal et al. |
| 2004/0098815 A1 | 5/2004 | Schmenger et al. |
| 2004/0107513 A1 | 6/2004 | Vidal et al. |
| 2004/0127692 A1 | 7/2004 | David et al. |
| 2004/0133995 A1 | 7/2004 | Cottard et al. |
| 2004/0141943 A1 | 7/2004 | Mougin et al. |
| 2004/0143911 A1 | 7/2004 | Vidal |
| 2004/0168263 A1 | 9/2004 | Vidal |
| 2004/0172771 A1 | 9/2004 | Cottard et al. |
| 2004/0180030 A1 | 9/2004 | Maubru |
| 2004/0187225 A1 | 9/2004 | Vidal et al. |
| 2004/0200009 A1 | 10/2004 | Vidal |
| 2004/0205902 A1 | 10/2004 | Cottard et al. |
| 2004/0216246 A1 | 11/2004 | Cotteret et al. |
| 2004/0244123 A1 | 12/2004 | Vidal et al. |
| 2005/0000039 A1 | 1/2005 | Audousset |
| 2005/0039268 A1 | 2/2005 | Plos et al. |
| 2005/0081311 A1 | 4/2005 | Schmenger et al. |

FOREIGN PATENT DOCUMENTS

| | | |
|---|---|---|
| EP | 0 122 324 | 10/1984 |
| EP | 0 080 976 | 9/1986 |
| EP | 0 412 706 | 2/1991 |
| EP | 0 337 354 | 2/1994 |
| EP | 0 825 200 | 2/1998 |
| EP | 1 048 289 | 11/2000 |
| EP | 1 142 555 | 10/2001 |
| EP | 1 174 450 | 1/2002 |
| EP | 0 824 914 | 2/2002 |
| EP | 1 232 739 | 8/2002 |
| EP | 0 714 954 | 9/2002 |
| EP | 1 413 287 | 4/2004 |
| EP | 1 426 032 | 6/2004 |
| EP | 1 426 039 | 6/2004 |
| EP | 1 428 506 | 6/2004 |
| EP | 1 473 025 | 11/2004 |
| EP | 1 518 547 | 3/2005 |
| FR | 1 400 366 | 5/1963 |
| FR | 1 492 597 | 8/1967 |
| FR | 1 583 363 | 10/1969 |
| FR | 2 077 143 | 10/1971 |
| FR | 2 080 759 | 11/1971 |
| FR | 2 162 025 | 7/1973 |
| FR | 2 190 406 | 2/1974 |
| FR | 2 252 840 | 6/1975 |
| FR | 2 270 846 | 12/1975 |
| FR | 2 280 361 | 2/1976 |
| FR | 2 316 271 | 1/1977 |
| FR | 2 320 330 | 3/1977 |
| FR | 2 336 434 | 7/1977 |
| FR | 2 368 508 | 5/1978 |
| FR | 2 383 660 | 10/1978 |
| FR | 2 393 573 | 1/1979 |
| FR | 2 413 907 | 8/1979 |
| FR | 2 470 596 | 6/1981 |
| FR | 2 505 348 | 11/1982 |
| FR | 2 519 863 | 7/1983 |
| FR | 2 542 997 | 9/1984 |
| FR | 2 598 611 | 11/1987 |
| FR | 2 692 572 | 12/1993 |
| FR | 2 717 076 | 9/1995 |
| FR | 2 795 312 | 12/2000 |
| FR | 2 803 195 | 7/2001 |
| FR | 2 807 650 | 10/2001 |
| FR | 2 822 693 | 10/2002 |
| FR | 2 822 694 | 10/2002 |
| FR | 2 822 696 | 10/2002 |
| FR | 2 822 698 | 10/2002 |
| FR | 2 825 625 | 12/2002 |
| FR | 2 825 702 | 12/2002 |
| FR | 2 829 926 | 3/2003 |
| FR | 2 833 833 | 6/2003 |
| FR | 2 844 269 | 3/2004 |
| GB | 1021400 | 3/1966 |
| GB | 1 331 819 | 9/1973 |
| GB | 1 347 051 | 2/1974 |
| GB | 1 479 786 | 7/1977 |
| GB | 1 546 809 | 5/1979 |
| WO | WO 95/01772 | 1/1995 |
| WO | WO 95/15144 | 6/1995 |
| WO | WO 99/40893 | 8/1999 |
| WO | WO 00/68282 | 11/2000 |
| WO | WO 02/30370 | 4/2002 |
| WO | WO 02/45674 | 6/2002 |
| WO | WO 02/074271 | 9/2002 |
| WO | WO 02/078660 | 10/2002 |
| WO | WO 02/100369 | 12/2002 |

| | | |
|---|---|---|
| WO | WO 02/100834 | 12/2002 |
| WO | WO 2004/019895 A1 | 3/2004 |

OTHER PUBLICATIONS

English Language Derwent Abstract for FR 2 470 596. (Jun. 1981).
English Language Derwent Abstract for FR 2 336 434. (Jul. 1977).
English Language Derwent Abstract for EP 0 080 976 (Sep. 1986).
Bruin, "Hydrophobically Modified Cellulose Ether for Personal Care." SOFW-Journal Seifen, Oele, Fette, Wachse, Verlag fur Chemische Industri, Augsburg, DE, vol. 120, No. 15, Nov. 30, 1994, pp. 944-946, 948, XP000483287, ISSN: 0942-7694.
U.S. Appl. No. 11/393,696, filed Mar. 31, 2006.
U.S. Appl. No. 11/393,698, filed Mar. 31, 2006.
U.S. Appl. No. 11/393,700, filed Mar. 31, 2006.
U.S. Appl. No. 11/393,701, filed Mar. 31, 2006.
U.S. Appl. No. 11/394,234, filed Mar. 31, 2006.
English language Derwent Abstract of DE 101 32 915, dated Jan. 30, 2003.
English language Dement Abstract of DE 41 27 230, dated Feb. 18, 1993.
English language Derwent Abstract of EP 1 232 739, dated Aug. 21, 2002.
English language Abstract of FR 1 400 366, dated May 15, 1963.
English language Derwent Abstract of FR 2 795 312, dated Dec. 29, 2000.
European Search Report for EP 06 11 1856 (corresponding European counterpart application to U.S. Appl. No. 11/394,234, dated Jul. 19, 2006.
European Search Report for EP 06 11 1858 (corresponding European counterpart application to U.S. Appl. No. 11/393,698, dated Jul. 19, 2006.
European Search Report for EP 06 11 1860 (corresponding European counterpart application to U.S. Appl. No. 11/393,701, dated Jul. 18, 2006.
French Search Report for FR 05/50835 for U.S. Appl. No. 11/393,700, dated Nov. 3, 2005.
French Search Report for FR 05/50838 for U.S. Appl. No. 11/393,698, dated Nov. 4, 2005.
French Search Report for FR 05/50839 for U.S. Appl. No. 11/393,701, dated Nov. 9, 2005.
French Search Report for FR 05/50841 for U.S. Appl. No. 11/393,696, dated Feb. 14, 2006.
French Search Report for FR 05/50842 for U.S. Appl. No. 11/394,234, dated Feb. 15, 2006.
G. Fonnum, J. Bakke and Fk. Hansen - Colloid Polym. Sci. 271, 380-389 (1993).
Office Action mailed Jan. 7, 2008, in co-pending U.S. Appl. No. 11/393,696.
Office Action mailed Jan. 7, 2008, in co-pending U.S. Appl. No. 11/393,698.
Office Action mailed Jan. 7, 2008, in co-pending U.S. Appl. No. 11/393,700.
Office Action mailed Jan. 7, 2008, in co-pending U.S. Appl. No. 11/393,701.
Office Action mailed Jan. 7, 2008, in co-pending U.S. Appl. No. 11/394,234.
Office Action mailed Jun. 13, 2008, in co-pending U.S. Appl. No. 11/393,698.
Office Action mailed Jun. 18, 2008, in co-pending U.S. Appl. No. 11/393,700.
Office Action mailed Jun. 23, 2008, in co-pending U.S. Appl. No. 11/394,234.
Office Action mailed Jun. 27, 2008, in co-pending U.S. Appl. No. 11/393,701.
Office Action mailed Oct. 22, 2008, in co-pending U.S. Appl. No. 11/393,698.

* cited by examiner

US 7,651,533 B2

DYE COMPOSITION WITH A REDUCED CONTENT OF STARTING MATERIALS, PROCESS FOR DYEING KERATIN FIBERS USING THE SAME AND DEVICE THEREFOR

CROSS-REFERENCE TO RELATED APPLICATIONS

This application claims benefit of U.S. Provisional Application No. 60/681,171, filed May 16, 2005, the contents of which are incorporated herein by reference. This application also claims benefit of priority under 35 U.S.C. § 119 to French Patent Application No. FR 05 50837, filed Mar. 31, 2005, the contents of which are also incorporated herein by reference.

FIELD OF THE INVENTION

The present disclosure relates to a dye composition comprising at least one dye, at least one nonionic surfactant, at least one anionic surfactant, at least one fatty alcohol and at least one fatty acid ester; the fatty alcohol/surfactant(s) weight ratio being greater than 0.5 and the water content being at least 55% by weight.

The present disclosure similarly relates to a process for dyeing keratin fibers, for example human keratin fibers, using such a composition, and also to a multi-compartment device comprising a dye composition in one compartment, and an oxidizing composition in another compartment.

BACKGROUND OF THE INVENTION

There are essentially two types of dyeing for keratin fibers, for example human keratin fibers such as the hair.

The first, known as oxidation dyeing or permanent dyeing, comprises using oxidation dye precursors, which are colorless or sparingly colored compounds. When they are placed in contact with an oxidizing agent, these compounds produce, via a process of oxidative condensation taking place within the fiber itself, colored substances that remain trapped in the fibers.

The second, known as direct dyeing or semi-permanent dyeing, is obtained by using colored and coloring compounds that have affinity for the keratin fibers onto which they are applied. This type of dyeing does not require the use of an oxidizing agent to reveal the color, although it is not excluded for this type of agent to be present during the process. The latter case is then referred to as lightening direct dyeing.

The dye compositions of the prior art are, in the majority of cases, in the form of liquids, gels or creams, which are mixed, if necessary, before being applied to fibers, with an oxidizing composition.

Dye compositions are usually relatively rich in starting materials, among which are usually found fatty substances, surfactants and/or polymers. These compositions are typically formulated such that they have spreading properties and textures that are easy to work in order to allow quick and easy application to fibers, while at the same time being thick enough not to run beyond the areas that it is desired to color. Furthermore, these compositions should ideally remain stable during the leave-on time on the fibers and should ideally be easy to remove by rinsing once the coloration has been obtained.

It is not uncommon to find that large amounts of starting materials penalize the dyeing qualities of such compositions. Less favorable kinetics, a reduced intensity of the shade obtained, poorer homogeneity of the color from one fiber to another and/or depending on the location of the fiber (root/end), etc. may thus be observed.

SUMMARY OF THE INVENTION

Thus, the present disclosure proposes dye compositions that avoid at least one of the abovementioned drawbacks of the current dye compositions, while at the same time preserving at least one of the properties mentioned above.

DETAILED DESCRIPTION OF THE INVENTION

Accordingly, disclosed herein are dye compositions comprising, in a medium that is suitable for dyeing keratin fibers:
 at least one dye chosen from oxidation dye precursors and direct dyes;
 at least one alkoxylated and/or glycerolated nonionic surfactant;
 at least one anionic surfactant;
 at least one fatty alcohol;
 at least one non-ethoxylated fatty acid ester of a $C_1$-$C_{10}$ alcohol;
 wherein the weight ratio of the total amount of fatty alcohols to the total amount of nonionic and anionic surfactants is greater than 0.5;
 and wherein the dye composition comprises water in an amount of at least 55% by weight relative to the total weight of the composition.

Also disclosed herein is a process for dyeing keratin fibers using such a composition, and, where appropriate, in the presence of an oxidizing composition.

Finally, the present disclosure relates to a device comprising a first compartment comprising a dye composition according to the disclosure and a second compartment comprising an oxidizing composition.

The composition according to the present disclosure may cause less degradation of the dyeing properties and allow stronger, more homogeneous and more chromatic colorations to be obtained, while at the same time giving the treated fibers good cosmetic properties and limiting their degradation.

The compositions in accordance with the present disclosure moreover may have an ideal texture for use in the dyeing of human keratin fibers, such as the hair. Specifically, they may be creamy, thick enough for quick and easy application, with good removal by rinsing, without, however, running beyond the areas of the hair that it is desired to treat.

Other characteristics and advantages of the disclosure will be more apparent after reading the description and the examples that follow.

In the text hereinbelow, and unless otherwise indicated, it is pointed out that the limits of ranges of values are included in these ranges.

When mention is made herein of a compound with a fatty chain, this chain is a linear or branched, saturated or unsaturated hydrocarbon-based chain comprising from 8 to 30 carbon atoms and, for example, from 10 to 24 carbon atoms.

Furthermore, the present disclosure is suitable for dyeing keratin fibers, for example human keratin fibers, such as the hair.

Thus, as has been indicated previously, the dye composition according to the disclosure comprises water in an amount of at least 55% by weight relative to the total weight of the dye composition.

According to at least one embodiment of the present disclosure, the water content comprises at least 60% by weight relative to the total weight of the said dye composition.

The composition according to the disclosure moreover comprises at least one alkoxylated and/or glycerolated nonionic surfactant.

The nonionic surfactant may be chosen from:
oxyalkylenated or glycerolated fatty alcohols;
oxyalkylenated alkylphenols chosen from $C_8$-$C_{18}$ alkyl chains;
oxyalkylenated or glycerolated fatty amides;
oxyalkylenated plant oils;
optionally oxyalkylenated $C_6$-$C_{30}$ acid esters of sorbitan;
optionally oxyalkylenated fatty acid esters of sucrose;
fatty acid esters of polyethylene glycol;
($C_6$-$C_{30}$)alkylpolyglycosides;
N—($C_6$-$C_{30}$)alkylglucamine derivatives;
amine oxides such as ($C_{10}$-$C_{14}$)alkylamine oxides or N-acylaminopropylmorpholine oxides;
copolymers of ethylene oxide and of propylene oxide; and mixtures thereof.

In at least one embodiment, the mean number of oxyalkylene units may range from 2 to 150 units. For example, the units may be oxyethylene units, oxypropylene units, and mixtures thereof.

The polyglycerolated surfactants may comprise on average 1 to 20, for example from 1.5 to 5, glycerol groups.

According to yet another embodiment of the present disclosure, the composition comprises at least one nonionic surfactant chosen from oxyalkylenated $C_6$-$C_{30}$ alcohols and glycerolated $C_6$-$C_{30}$ alcohols.

The at least one nonionic surfactant is present in the composition in an amount ranging from 0.01% to 50% by weight relative to the total weight of the dye composition, such as from 0.5% to 40% by weight relative to the total weight of the dye composition.

The composition also comprises at least one anionic surfactant. These surfactants may be chosen from:
($C_6$-$C_{30}$)alkyl sulfates, ($C_6$-$C_{30}$)alkyl ether sulfates, ($C_6$-$C_{30}$)alkylamido ether sulfates, alkylaryl polyether sulfates, monoglyceride sulfates;
($C_6$-$C_{30}$)alkylsulfonates, ($C_6$-$C_{30}$)alkylamide sulfonates, ($C_6$-$C_{30}$)alkylaryl sulfonates, α-olefin sulfonates, paraffin sulfonates;
($C_6$-$C_{30}$)alkyl phosphates;
($C_6$-$C_{30}$)alkyl sulfosuccinates, ($C_6$-$C_{30}$)alkyl ether sulfosuccinates, ($C_6$-$C_{30}$)alkylamide sulfosuccinates;
($C_6$-$C_{30}$)alkyl sulfoacetates;
($C_6$-$C_{24}$)acyl sarcosinates;
($C_6$-$C_{24}$)acyl glutamates;
($C_6$-$C_{30}$)alkylpolyglycoside carboxylic ethers; ($C_6$-$C_{30}$) alkylpolyglycoside sulfosuccinates;
($C_6$-$C_{30}$)alkyl sulfosuccinamates;
($C_6$-$C_{24}$)acyl isethionates;
N—($C_6$-$C_{24}$)acyl taurates;
fatty acid salts;
($C_8$-$C_{20}$)acyl lactylates;
($C_6$-$C_{30}$)alkyl-D-galactoside uronic acid salts;
polyoxyalkylenated($C_6$-$C_{30}$)alkyl ether carboxylic acid salts, polyoxyalkylenated($C_6$-$C_{30}$)alkylaryl ether carboxylic acid salts, polyoxyalkylenated($C_6$-$C_{30}$)alkylamido ether carboxylic acid salts;
and mixtures thereof.

According to at least one embodiment of the present disclosure, these anionic surfactants may be in the form of salts in the composition such as salts of alkali metals, for instance sodium; salts of alkaline-earth metals, for instance magnesium; ammonium salts; amine salts; and amino alcohol salts. Depending on the conditions, they may also be in the acid form thereof.

In at least one embodiment, the alkyl or acyl radicals of these various compounds may comprise from 12 to 20 carbon atoms. In addition, the aryl radical may be chosen from phenyl groups and benzyl groups.

Furthermore, the polyoxyalkylenated anionic surfactants may comprise from 2 to 50 alkylene oxide and, for example, ethylene oxide groups.

According to at least one embodiment of the present disclosure, the anionic surfactant is chosen from fatty acid salts.

The at least one anionic surfactant is present in the composition in an amount ranging from 0.01% to 50% by weight relative to the total weight of the dye composition, such as from 0.5% to 40% by weight relative to the total weight of the dye composition.

The composition moreover comprises at least one fatty alcohol.

This fatty alcohol may be non-oxyalkylenated and non-glycerolated.

The fatty alcohol may be chosen from linear or branched, saturated or unsaturated $C_8$-$C_{30}$, for example $C_{10}$-$C_{24}$, such as $C_{12}$-$C_{24}$, alcohols, optionally comprising at least one other hydroxyl group. Non-limiting examples that may be mentioned, inter alia, include oleyl alcohol, lauryl alcohol, palmityl alcohol, myristyl alcohol, behenyl alcohol, stearyl alcohol, linoleyl alcohol, linolenyl alcohol, capryl alcohol, arachidonyl alcohol, and mixtures thereof.

According to at least one embodiment of the present disclosure, the at least one fatty alcohol is present in the composition in an amount ranging from 0.1% to 30% by weight, such as from 0.5% to 20% by weight, relative to the total weight of the dye composition.

According to at least one embodiment of the present disclosure, the weight ratio of the total amount of fatty alcohols to the total amount of nonionic and anionic surfactants is greater than 0.5, for example, greater than 0.75.

According to at least one embodiment of the present disclosure, the composition may comprise another fatty substance other than the abovementioned fatty alcohols. Thus, the composition may comprise as fatty substance at least one compound chosen from non-oxyalkylenated and non-glycerolated fatty acid amides, mineral oils and plant oils, and mixtures thereof.

The fatty acid amides may be chosen from compounds derived from an alkanolamine and from a $C_8$-$C_{30}$ fatty acid. In at least one embodiment, they may be chosen from amides of a $C_2$-$C_{10}$ alkanolamine and of a $C_{14}$-$C_{30}$ fatty acid, and for example, from amides of a $C_2$-$C_{10}$ alkanolamine and of a $C_{14}$-$C_{22}$ fatty acid.

The fatty acid amide may be chosen from:
oleic acid diethanolamide, such as the amide sold under the trade name Mexanyl® GT by the company Chimex,
myristic acid monoethanolamide, such as the amide sold under the trade name Comperlan® MM by the company Cognis,
soybean fatty acid diethanolamide, such as the amide sold under the trade name Comperlan® VOD by the company Cognis,
stearic acid ethanolamide, such as the amide sold under the trade name Monamid® S by the company Uniqema,
oleic acid monoisopropanolamide, such as the amide sold under the trade name Witcamide® 61 by the company Witco,
linoleic acid diethanolamide, such as the amide sold under the trade name Purton® SFD by the company Zschimmer Schwarz, stearic acid monoethanolamide, such as the amide sold under the trade name Monamid® 972 by the company ICI/Uniqema, behenic acid monoethanolamide, such as the amide sold under the trade name Incromide® BEM from Croda, isostearic acid monoisopropanolamide, such as the amide sold under the trade name Witcamide® SPA by the company Witco, erucic acid diethanolamide, such as the amide sold under the trade name erucic acid diethanolamide by the company Stéarineries Dubois, ricinoleic acid monoethanolamide, such as the amide sold under the trade name ricinoleic monoethanolamide by the company Stéarineries Dubois.

Liquid paraffin is an example of a mineral oil that may be used as fatty substance in the composition.

According to one embodiment, mention may be made of the plant oils, such as avocado oil, olive oil or liquid jojoba wax.

In at least one embodiment of the present disclosure, the total amount of fatty substances other than the abovementioned fatty alcohols ranges from 0.1% to 30% by weight, such as from 0.5% to 20% by weight, of the total weight of the dye composition.

As has been mentioned previously, the composition also comprises at least one non-ethoxylated fatty acid ester of a $C_1$-$C_{10}$ alcohol.

The said ester may be a monoester, diester or triester of a linear or branched, saturated or unsaturated $C_8$-$C_{30}$ carboxylic acid and of a linear or branched, saturated or unsaturated $C_1$-$C_{10}$ monohydroxylated or polyhydroxylated alcohol, with the exception of monoethylene, diethylene and triethylene glycol.

For example, the ester may be chosen from the monoesters, diesters or triesters of oleic acid, lauric acid, palmitic acid, myristic acid, behenic acid, stearic acid, linoleic acid, linolenic acid, capric acid and arachidonic acid, and of methanol, ethanol, propanol, isopropanol, glycerol, octanol and decanol, and also mixtures thereof.

According to at least one embodiment of the present disclosure, the amount of fatty acid ester of a $C_1$-$C_{10}$ alcohol ranges from 0.1% to 20% by weight, such as from 0.5% to 15% by weight, relative to the total weight of the dye composition.

The composition according to the present disclosure also comprises at least one dye chosen from oxidation dye precursors and direct dyes.

The oxidation dye precursor(s) may be chosen from oxidation bases and couplers, and mixtures thereof.

The oxidation bases are chosen from the oxidation bases conventionally used for oxidation dyeing, among which non-limiting mention may be made of para-phenylenediamines, bis(phenyl)alkylenediamines, para-aminophenols, ortho-aminophenols and heterocyclic bases, and the addition salts thereof with an acid or with an alkaline agent.

Among the para-phenylenediamines non-limiting mention may be made of para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine and 4'-aminophenyl-1-(3-hydroxy)pyrrolidine, and the addition salts thereof with an acid or with an alkaline agent.

In at least one embodiment, the para-phenylenediamines are chosen from para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid or with an alkaline agent.

Among the bis(phenyl)alkylenediamines, non-limiting mention may be made of N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,5-dioxaoctane, and the addition salts thereof with an acid or with an alkaline agent.

Among the para-aminophenols, non-limiting mention may be made of para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid or with an alkaline agent.

Among the ortho-aminophenols, non-limiting mention may be made of 2-aminophenol, 2-amino-5-methylphenol, 2-amino-6-methylphenol and 5-acetamido-2-aminophenol, and the addition salts thereof with an acid or with an alkaline agent.

Among the heterocyclic bases, non-limiting mention may be made of pyridine derivatives, for example 2,3-diamino-6-methoxypyridine; pyrimidine derivatives such as, 2,4,5,6-tetraaminopyrimidine or 4-hydroxy-2,5,6-triaminopyrimidine; and pyrazole derivatives, such as 1N-β-hydroxyethyl-4,5-diaminopyrazole; and the addition salts thereof with an acid or with an alkaline agent.

When they are used, the oxidation base(s) are present in an amount ranging from 0.0005% to 12% by weight relative to the total weight of the dye composition, and for example from 0.005% to 6% by weight relative to the total weight of the dye composition.

The composition may also comprise, combined with at least one oxidation base, at least one coupler so as to modify or to enrich with tints the shades obtained.

The coupler(s) that may be used may be chosen from the couplers conventionally used in oxidation dyeing, and among which non-limiting mention may be made of meta-phenylenediamines, meta-aminophenols, meta-diphenols and heterocyclic couplers, and the addition salts thereof with an acid or with an alkaline agent.

For example, these couplers may be chosen from 2-methyl-5-aminophenol, 5-N-(β-hydroxyethyl)amino-2-methylphenol, 3-aminophenol, 2-methyl-5-amino-6-chlorophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxy-ethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2-amino-3-hydroxypyridine, 2,6-dihydroxy-4-methylpyridine, 1H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole and 6-methylpyrazolo[1,5-a]benzimidazole, and the addition salts thereof with an acid or with an alkaline agent.

When they are present, the amount of the coupler(s) in the composition ranges from 0.0001% to 15% by weight relative to the total weight of the dye composition and for example, from 0.005% to 12% by weigh, such as from 0.01% to 10% by weight relative to the total weight of the dye composition.

In general, the addition salts with an acid may be chosen from the hydrochlorides, hydrobromides, sulfates, citrates, succinates, tartrates, tosylates, benzenesulfonates, lactates and acetates.

The direct dye(s) used herein may be of nonionic, cationic or anionic nature.

Non-limiting examples of direct dyes that may be mentioned include nitrobenzene dyes, azo, azomethine, methine, tetraazapentamethine, anthraquinone, naphthoquinone, benzoquinone, phenothiazine, indigoid, xanthene, phenanthridine, phthalocyanin and triarylmethane-based dyes and natural dyes, alone and as mixtures.

The direct dye(s) may be chosen, for example, from the following red or orange nitrobenzene dyes:
 1-hydroxy-3-nitro-4-N-(γ-hydroxypropyl)aminobenzene,
 N-(β-hydroxyethyl)amino-3-nitro-4-aminobenzene,
 1-amino-3-methyl-4-N-(β-hydroxyethyl)amino-6-nitrobenzene,
 1-hydroxy-3-nitro-4-N-(β-hydroxyethyl)aminobenzene,
 1,4-diamino-2-nitrobenzene,
 1-amino-2-nitro-4-methylaminobenzene,
 N-(β-hydroxyethyl)-2-nitro-para-phenylenediamine,
 1-amino-2-nitro-4-(β-hydroxyethyl)amino-5-chlorobenzene,
 2-nitro-4-aminodiphenylamine,
 1-amino-3-nitro-6-hydroxybenzene,
 1-(β-aminoethyl)amino-2-nitro-4-(β-hydroxyethyloxy)benzene,
 1-(β,γ-dihydroxypropyl)oxy-3-nitro-4-(β-hydroxyethyl)aminobenzene,
 1-hydroxy-3-nitro-4-aminobenzene,
 1-hydroxy-2-amino-4,6-dinitrobenzene,
 1-methoxy-3-nitro-4-(β-hydroxyethyl)aminobenzene,
 2-nitro-4'-hydroxydiphenylamine, and
 1-amino-2-nitro-4-hydroxy-5-methylbenzene.

The direct dye may also be chosen from yellow and green-yellow nitrobenzene direct dyes; mention may be made, for example, of the compounds chosen from:
 1-β-hydroxyethyloxy-3-methylamino-4-nitrobenzene,
 1-methylamino-2-nitro-5-(β,γ-dihydroxypropyl)oxybenzene,
 1-(β-hydroxyethyl)amino-2-methoxy-4-nitrobenzene,
 1-(β-aminoethyl)amino-2-nitro-5-methoxybenzene,
 1,3-di(β-hydroxyethyl)amino-4-nitro-6-chlorobenzene,
 1-amino-2-nitro-6-methylbenzene,
 1-(β-hydroxyethyl)amino-2-hydroxy-4-nitrobenzene,
 N-(β-hydroxyethyl)-2-nitro-4-trifluoromethylaniline,
 4-(β-hydroxyethyl)amino-3-nitrobenzenesulfonic acid,
 4-ethylamino-3-nitrobenzoic acid,
 4-(β-hydroxyethyl)amino-3-nitrochlorobenzene,
 4-(β-hydroxyethyl)amino-3-nitromethylbenzene,
 4-(β,γ-dihydroxypropyl)amino-3-nitrotrifluoromethylbenzene,
 1-(β-ureidoethyl)amino-4-nitrobenzene,
 1,3-diamino-4-nitrobenzene,
 1-hydroxy-2-amino-5-nitrobenzene,
 1-amino-2-[tris(hydroxymethyl)methyl]amino-5-nitrobenzene,
 1-(β-hydroxyethyl)amino-2-nitrobenzene, and
 4-(β-hydroxyethyl)amino-3-nitrobenzamide.

Non-limiting mention may also be made of blue or violet nitrobenzene direct dyes, for instance:
 1-(β-hydroxyethyl)amino-4-N,N-bis(β-hydroxyethyl)amino-2-nitrobenzene,
 1-(γ-hydroxypropyl)amino-4,N,N-bis(β-hydroxyethyl)amino-2-nitrobenzene,
 1-(β-hydroxyethyl)amino-4-(N-methyl-N-β-hydroxyethyl)amino-2-nitrobenzene,
 1-(β-hydroxyethyl)amino-4-(N-ethyl-N-β-hydroxyethyl)amino-2-nitrobenzene,
 1-(β,γ-dihydroxypropyl)amino-4-(N-ethyl-N-β-hydroxyethyl)amino-2-nitrobenzene,
 2-nitro-para-phenylenediamines having the following formula:

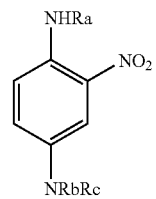

wherein:
 Rb is chosen from $C_1$-$C_4$ alkyl radicals and from β-hydroxyethyl, β-hydroxypropyl and γ-hydroxypropyl radicals;
 Ra and Rc, which may be identical or different, are chosen from β-hydroxyethyl, β-hydroxypropyl, γ-hydroxypropyl and β,γ-dihydroxypropyl radicals, wherein at least one of the radicals Rb, Rc or Ra is chosen from γ-hydroxypropyl radicals and Ra and Rc are not simultaneously able to denote β-hydroxyethyl radicals when Rb is a γ-hydroxypropyl radical, such as those described in French Patent No. 2 692 572.

Among the azo direct dyes that may be used according to the disclosure, non-limiting mention may be made of the cationic azo dyes described in PCT Published Application Nos. 95/15144 and 95/01772, European Patent No. 714 954, French Patent Nos. 2 822 696, 2 825 702, 2 825 625, 2 822 698, 2 822 693, 2 822 694, 2 829 926, 2 807 650, 2 844 269, and PCT Published Application Nos. 02/078 660, 02/100 834, and 02/100 369.

Among these compounds, non-limiting mention may be made of the following dyes:
 1,3-dimethyl-2-[[4-(dimethylamino)phenyl]azo]-1H-imidazolium chloride,
 1,3-dimethyl-2-[(4-aminophenyl)azo]-1H-imidazolium chloride,
 1-methyl-4-[(methylphenylhydrazono)methyl]pyridinium methyl sulfate.

Among the azo direct dyes, non-limiting mention may be made of the following dyes described in the Colour Index International 3rd edition: Disperse Red 17, Acid Yellow 9, Acid Black 1, Basic Red 22, Basic Red 76, Basic Yellow 57, Basic Brown 16, Acid Yellow 36, Acid Orange 7, Acid Red 33, Acid Red 35, Basic Brown 17, Acid Yellow 23, Acid Orange 24, Disperse Black 9.

Non-limiting mention may also be made of 1-(4'-aminodiphenylazo)-2-methyl-4-[bis(β-hydroxyethyl)amino]Benzene and 4-hydroxy-3-(2-methoxyphenylazo)-1-naphthalenesulfonic acid.

Among the quinone direct dyes, non-limiting mention may be made of the following dyes: Disperse Red 15, Solvent Violet 13, Acid Violet 43, Disperse Violet 1, Disperse Violet 4, Disperse Blue 1, Disperse Violet 8, Disperse Blue 3, Disperse Red 11, Acid Blue 62, Disperse Blue 7, Basic Blue 22, Disperse Violet 15, Basic Blue 99. Non-limiting mention may also be made of the following compounds:

1-N-methylmorpholiniumpropylamino-4-hydroxyanthraquinone
1-aminopropylamino-4-methylaminoanthraquinone
1-aminopropylaminoanthraquinone
5-β-hydroxyethyl-1,4-diaminoanthraquinone
2-aminoethylaminoanthraquinone
1,4-bis(β,γ-dihydroxypropylamino)anthraquinone.

Among the azine dyes, non-limiting mention may be made of the following compounds: Basic Blue 17, Basic Red 2.

Among the cationic methine direct dyes, non-limiting mention may also be made of Basic Red 14, Basic Yellow 13 and Basic Yellow 29.

Among the triarylmethane dyes that may be used according to the disclosure, non-limiting mention may be made of the following compounds: Basic Green 1, Acid Blue 9, Basic Violet 3, Basic Violet 14, Basic Blue 7, Acid Violet 49, Basic Blue 26, Acid Blue 7.

Among the indoamine dyes that may be used according to the disclosure, non-limiting mention may be made of the following compounds:

2-β-hydroxyethylamino-5-[bis(β-4'-hydroxyethyl)amino]anilino-1,4-benzoquinone;
2-β-hydroxyethylamino-5-(2'-methoxy-4'-amino)anilino-1,4-benzoquinone;
3-N(2'-chloro-4'-hydroxy)phenylacetylamino-6-methoxy-1,4-benzoquinoneimine;
3-N(3'-chloro-4'-methylamino)phenylureido-6-methyl-1,4-benzoquinoneimine;
3-[4'-N-(ethylcarbamylmethyl)amino]phenylureido-6-methyl-1,4-benzoquinoneimine.

The composition may also comprise natural direct dyes, for instance lawsone, juglone, alizarin, purpurin, carminic acid, kermesic acid, purpurogallin, protocatechaldehyde, indigo, isatin, curcumin, spinulosin or apigenidin. Extracts or decoctions comprising these natural dyes, for example henna-based poultices or extracts, may also be used.

The direct dye(s), when present, are present in an amount ranging from 0.0005% to 15% by weight relative to the total weight of the dye composition, and for example from 0.005% to 12%, such as from 0.01% to 5%, by weight relative to the total weight of the dye composition.

The composition according to the disclosure may also comprise at least one basifying agent.

Among the basifying agents, non-limiting mention may be made of aqueous ammonia, alkali metal carbonates, $C_2$-$C_{10}$ alkanolamines such as monoethanolamine, diethanolamine and triethanolamine and also derivatives thereof, oxyethylenated and/or oxypropylenated hydroxyalkylamines and ethylenediamines, sodium hydroxide, potassium hydroxide, alkali metal or alkaline-earth metal silicates and the compounds having the following formula:

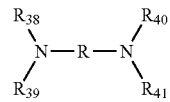

wherein R is a propylene residue optionally substituted with hydroxyl groups or $C_1$-$C_4$ alkyl radicals; $R_{38}$, $R_{39}$, $R_{40}$ and $R_{41}$, which may be identical or different, are chosen from hydrogen atoms, $C_1$-$C_4$ alkyl radicals and $C_1$-$C_4$ hydroxyalkyl radicals.

In at least one embodiment, the basifying agent is chosen from aqueous ammonia, alkanolamines and combinations of alkanolamines with alkali metal or alkaline-earth metal silicates.

According to one embodiment of the present disclosure, the composition does not comprise aqueous ammonia as basifying agent.

It should moreover be noted that the pH may also be adjusted by using acidifying agents, for instance mineral or organic acids such as hydrochloric acid, orthophosphoric acid or sulfuric acid, carboxylic acids, for instance acetic acid, tartaric acid, citric acid or lactic acid, or sulfonic acids.

The basifying and/or acidifying agent is present in the composition in an amount such that the pH of the dye composition ranges from 3 to 12, for example from 4 to 11, such as from 7 to 11.

The composition according to the disclosure may also comprise at least one cationic or amphoteric substantive polymer.

It should be noted that, for the purposes of the present disclosure, the term "cationic polymer" denotes any polymer comprising cationic groups and/or groups that may be ionized into cationic groups.

Such polymers may be chosen from those already known per se as improving the cosmetic properties of the hair, i.e., especially those described in European Patent Application No.-A-337 354 and in French Patent Nos. 2 270 846, 2 383 660, 2 598 611, 2 470 596 and 2 519 863.

The cationic polymers may be chosen from those units comprising primary, secondary, tertiary and/or quaternary amine groups, which may either form part of the main polymer chain or may be borne by a side substituent directly attached thereto.

The cationic polymers used generally have a number-average molecular mass ranging from 500 to $5\times10^6$ such as from $10^3$ to $3\times10^6$.

Among the cationic polymers, non-limiting mention may be made of polymers of the polyamine, polyamino amide and polyquaternary ammonium type.

These are known products and are described, for instance, in French Patents Nos 2 505 348 and 2 542 997. Among the said polymers, non-limiting mention may be made of:

(1) homopolymers or copolymers derived from acrylic or methacrylic esters or amides and comprising at least one of the units of formula (I), (II), (III) or (IV) below:

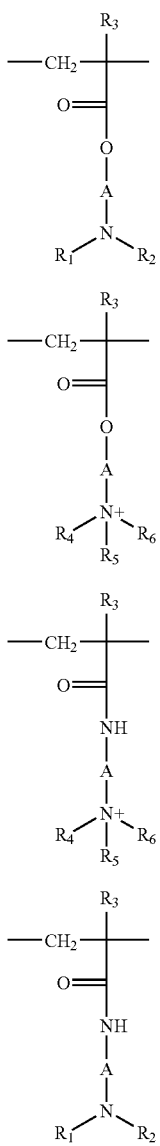

wherein:

R$_3$, which may be identical or different, is chosen from hydrogen atoms and a CH$_3$ radical;

A, which may be identical or different, is chosen from linear or branched alkyl groups of 1 to 6 carbon atoms, for example 2 or 3 carbon atoms, and hydroxyalkyl groups of 1 to 4 carbon atoms;

R$_4$, R$_5$ and R$_6$, which may be identical or different, are chosen from alkyl groups comprising 1 to 18 carbon atoms or benzyl radicals and for example, alkyl groups comprising 1 to 6 carbon atoms;

R$_1$ and R$_2$, which may be identical or different, are chosen from hydrogen and from an alkyl groups comprising from 1 to 6 carbon atoms, for example methyl or ethyl;

X is chosen from anions derived from inorganic or organic acids, such as a methosulfate anion or a halide such as chloride or bromide.

The polymers of family (1) can also comprise at least one unit derived from comonomers which may be chosen from the family of acrylamides, methacrylamides, diacetone acrylamides, acrylamides and methacrylamides substituted on the nitrogen with lower (C$_1$-C$_4$)alkyls, acrylic or methacrylic acids or esters thereof, vinyllactams such as vinylpyrrolidone or vinylcaprolactam, and vinyl esters.

Thus, among these polymers of family (1), non-limiting mention may be made of:

copolymers of acrylamide and of dimethylaminoethyl methacrylate quaternized with dimethyl sulfate or with a dimethyl halide, such as the product sold under the name HERCOFLOC by the company Hercules, the copolymers of acrylamide and of methacryloyloxyethyltrimethylammonium chloride described, for example, in European Patent Application No. 080 976 and sold under the name BINA QUAT P 100 by the company Ciba Geigy, the copolymer of acrylamide and of methacryloyloxyethyltrimethylammonium methosulfate sold under the name RETEN by the company Hercules, quaternized or non-quaternized vinylpyrrolidone/dialkylaminoalkyl acrylate or methacrylate copolymers, such as the products sold under the name "Gafquat" by the company ISP, for instance "Gafquat 734" or "Gafquat 755", or alternatively the products known as "Copolymer 845, 958 and 937". These polymers are described in detail in French Patent Nos. 2 077 143 and 2 393 573, dimethylaminoethyl methacrylate/vinylcaprolactam/vinylpyrrolidone terpolymers, such as the product sold under the name GAFFIX VC 713 by the company ISP, vinylpyrrolidone/methacrylamidopropyidimethylamine copolymers sold under the name STYLEZE CC 10 by ISP, and quaternized vinylpyrrolidone/dimethylaminopropyl methacrylamide copolymers such as the product sold under the name "Gafquat HS 100" by the company ISP.

(2) The cellulose ether derivatives comprising quaternary ammonium groups, which are described in French Patent No.1 492 597, and the polymers sold under the names "JR" (JR 400, JR 125, JR 30M) or "LR" (LR 400, LR 30M) by the company Union Carbide Corporation. These polymers are also defined in the CTFA dictionary as hydroxyethylcellulose quaternary ammoniums that have reacted with an epoxide substituted with a trimethylammonium group.

(3) Cationic cellulose derivatives such as the copolymers of cellulose or cellulose derivatives grafted with a water-soluble quaternary ammonium monomer, described, for instance, in U.S. Pat. No. 4,131,576, such as hydroxyalkylcelluloses, for instance hydroxymethyl-, hydroxyethyl- or hydroxypropylcelluloses grafted with a methacryloylethyl-trimethylammonium, methacrylamidopropyltrimethylammonium and dimethyldiallylammonium salt. The commercial products corresponding to this definition are the products sold under the names CELQUAT L 200 and CELQUAT H 100 by the company National Starch.

(4) The cationic guar gums described for example in U.S. Pat. Nos. 3,589,578 and 4,031,307, such as guar gums comprising trialkylammonium cationic groups. Guar gums may be, for example, modified with a salt (e.g. chloride) of 2,3-epoxypropyltrimethyl-ammonium.

Such products are sold under the trade names JAGUAR C13S, JAGUAR C15, JAGUAR C17 and JAGUAR C162 by the company Meyhall.

(5) Polymers comprising of piperazinyl units and of divalent alkylene or hydroxyalkylene radicals comprising straight or branched chains, optionally interrupted by oxygen, sulfur or nitrogen atoms or by aromatic or heterocyclic rings, and also the oxidation and/or quaternization products of these polymers. Such polymers are described, for instance, in French Patent Nos. 2 162 025 and 2 280 361.

(6) Water-soluble polyamino amides prepared for example by polycondensation of an acidic compound with a polyamine; these polyamino amides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative; the crosslinking agent being used in amounts ranging from 0.025 to 0.35 mol per amine group of the polyamino amide; these polyamino amides can be alkylated or, if they contain one or more tertiary amine functions, they can be quaternized. Such polymers are described, for example, in French Patent Nos. 2 252 840 and 2 368 508.

(7) The polyamino amide derivatives resulting from the condensation of polyalkylene polyamines with polycarboxylic acids followed by alkylation with difunctional agents. Non-limiting mention may be made of adipic acid/dialkylaminohydroxyalkyl-dialkylenetriamine polymers wherein the alkyl radicals comprise from 1 to 4 carbon atoms and for example methyl, ethyl or propyl. Such polymers are described, for instance, in French Patent No. 1 583 363.

Among these derivatives, non-limiting mention may be made of the adipic acid/dimethylaminohydroxypropyl/diethylenetriamine polymers sold under the name "Cartaretine F, F4 or F8" by the company Sandoz.

(8) The polymers obtained by reaction of a polyalkylene polyamine comprising two primary amine groups and at least one secondary amine group with a dicarboxylic acid chosen from diglycolic acid and saturated aliphatic dicarboxylic acids comprising 3 to 8 carbon atoms. The molar ratio between the polyalkylene polyamine and the dicarboxylic acid ranges from 0.8:1 to 1.4:1; the polyamino amide resulting therefrom is reacted with epichlorohydrin in a molar ratio of epichlorohydrin relative to the secondary amine group of the polyamino amide ranging from 0.5:1 to 1.8:1. Such polymers are described, for instance, in U.S. Pat. Nos. 3,227,615 and 2,961,347.

Polymers of this type are sold under the name "Hercosett 57" by the company Hercules Inc. or alternatively under the name "PD 170" or "Delsette 101" by the company Hercules in the case of the adipic acid/epoxypropyl/diethylenetriamine copolymer.

(9) Cyclopolymers of alkyldiallylamine or of dialkyldiallylammonium, such as the homopolymers or copolymers comprising, as main constituent of the chain, units corresponding to formula (V) or (VI):

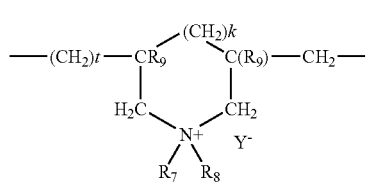

(V)

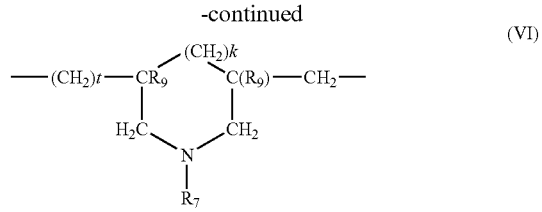

(VI)

in which formulae
k and t are equal to 0 or 1, the sum k+t being equal to 1;
$R_9$ is chosen from a hydrogen atom and a methyl radical;
$R_7$ and $R_8$, independently of each other, are chosen from alkyl groups comprising 1 to 6 carbon atoms, for example, 1 to 4 carbon atoms, hydroxyalkyl groups wherein the alkyl groups have, for example, 1 to 5 carbon atoms, lower ($C_1$-$C_4$)amidoalkyl groups, or $R_7$ and $R_8$ may form, together with the nitrogen atoms to which they are attached, heterocyclic groups such as piperidyl or morpholinyl;
$Y^-$ is chosen from anions such as bromide, chloride, acetate, borate, citrate, tartrate, bisulfate, bisulfite, sulfate or phosphate.

These polymers are described, for instance, in French Patent No. 2 080 759 and in its Certificate of Addition 2 190 406.

Among the polymers defined above, non-limiting mention may be made of the dimethyldiallylammonium chloride homopolymer sold under the name "Merquat 100" by the company Calgon (and its homologues of low weight-average molecular mass) and the copolymers of diallyldimethylammonium chloride and of acrylamide, sold under the name "Merquat 550".

(10) The quaternary diammonium polymer comprising repeating units corresponding to the formula:

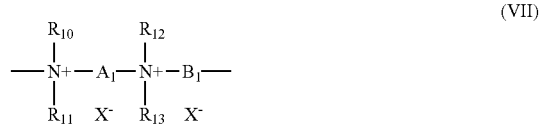

(VII)

in which formula (VII):
$R_{10}$, $R_{11}$, $R_{12}$ and $R_{13}$, which may be identical or different, are chosen from aliphatic, alicyclic and arylaliphatic radicals comprising 1 to 20 carbon atoms or lower hydroxyalkylaliphatic radicals, or alternatively $R_{10}$, $R_{11}$, $R_{12}$ and $R_{13}$, together or separately, constitute, with the nitrogen atoms to which they are attached, heterocycles optionally comprising a second hetero atom other than nitrogen, or alternatively $R_{10}$, $R_{11}$, $R_{12}$ and $R_{13}$ are chosen from linear or branched $C_1$-$C_6$ alkyl radicals substituted with a group chosen from nitriles, esters, acyls and amide groups and a group —CO—O—$R_{14}$-D or —CO—NH—$R_{14}$-D where $R_{14}$ is an alkylene and D is a quaternary ammonium groups;

$A_1$ and $B_1$ are chosen from polymethylene groups comprising 2 to 20 carbon atoms which may be linear or branched, saturated or unsaturated, and which may comprise, linked to or intercalated in the main chain, at least one aromatic ring or at least one oxygen or sulfur atom or at least one group chosen from sulfoxide, sulfone, disulfide, amino, alkylamino, hydroxyl, quaternary ammonium, ureido, amide and ester groups, and $X^-$ is chosen from anions derived from an inorganic or organic acid;

$A_1$, $R_{10}$ and $R_{12}$ can form, with the two nitrogen atoms to which they are attached, a piperazine ring; in addition, if $A_1$ is chosen from linear or branched, saturated or unsaturated alkylene or hydroxyalkylene radicals, $B_1$ can also be chosen from a group $-(CH_2)_n-CO-D-OC-(CH_2)_n-$ wherein D is chosen from:
- a) a glycol residue of formula: $-O-Z-O-$, where Z is chosen from linear or branched hydrocarbon-based radicals and from groups corresponding to one of the following formulae:

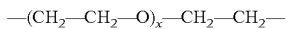

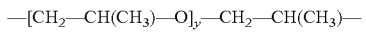

where x and y are, independently, integers from 1 to 4, representing a defined and unique degree of polymerization or any number from 1 to 4, representing an average degree of polymerization;
- b) a bis-secondary diamine residue such as a piperazine derivative;
- c) a bis-primary diamine residue of formula: $-NH-Y-NH-$, where Y is chosen from linear or branched hydrocarbon-based radicals, or alternatively from divalent radicals

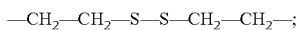

- d) ureylene groups of formula: $-NH-CO-NH-$.

$X^-$ is chosen from anions such as chloride or bromide.

These polymers generally have a number-average molecular mass ranging from 1000 to 100 000.

Polymers of this type are described, for instance, in French Patent Nos. 2 320 330, 2 270 846, 2 316 271, 2 336 434 and 2 413 907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

In at least one embodiment, it is possible to use polymers that comprise repeating units corresponding to the following formula (VIII):

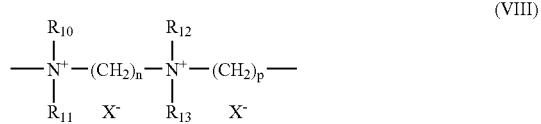

wherein
$R_{10}$, $R_{11}$, $R_{12}$ and $R_{13}$, which may be identical or different, are chosen from alkyl and hydroxyalkyl radicals comprising 1 to 4 carbon atoms,
n and p are, independently, integers ranging from 2 to 20, and
$X^-$ is, independently, an anion derived from a mineral or organic acid.

(11) Polyquaternary ammonium polymers comprising units of formula (IX)

wherein p is an integer ranging from 1 to 6, D is a bond or a group $-(CH_2)_r-CO-$ where r is a number equal to 4 or 7, and $X^-$ is an anion.

Such polymers may be prepared according to the processes described in U.S. Pat. Nos. 4,157,388, 4,702,906 and 4,719,282. They are also described in European Patent No.122 324.

Among these polymers, non-limiting examples that may be mentioned include the products "Mirapol A 15", "Mirapol AD1", "Mirapol AZ1" and "Mirapol 175" sold by the company Miranol.

(12) Quaternary polymers of vinylpyrrolidone and of vinylimidazole, for instance the products sold under the names LUVIQUAT FC 905, FC 550 and FC 370 by the company BASF.

(13) Polyamines such as POLYQUART H sold by Henkel, which is given under the reference name "Polyethylene glycol (15) tallow polyamine" in the CTFA dictionary.

(14) Crosslinked methacryloyloxy($C_1$-$C_4$)alkyltri($C_1$-$C_4$) alkylammonium salt polymers such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with a compound containing olefinic unsaturation, for example methylenebisacrylamide. A crosslinked acrylamide/methacryloyloxyethyltrimethylammonium chloride copolymer (20/80 by weight) in the form of a dispersion comprising 50% by weight of the said copolymer in mineral oil can be used in at least one embodiment. This dispersion is sold under the name "Salcare® SC 92" by the company Allied Colloids. A crosslinked meth-acryloyloxyethyltrimethylammonium chloride homopolymer comprising 50% by weight of the homopolymer in mineral oil or in a liquid ester can also be used. These dispersions are sold under the names "Salcare® SC 95" and "Salcare® SC 96" by the company Allied Colloids.

(15) Other cationic polymers which can be used in the context of the present disclosure are polyalkyleneimines, for example polyethyleneimines, polymers comprising vinylpyridine or vinylpyridinium units, condensates of polyamines and of epichlorohydrin, quaternary polyureylenes and chitin derivatives.

According to one embodiment of the present disclosure, the cationic polymers of families (1), (9), (10), (11) and (14) may be used. For example, the polymers comprising repeating units of formulae (W) and (U) below may be used:

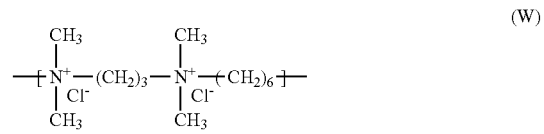

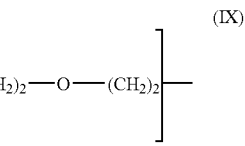

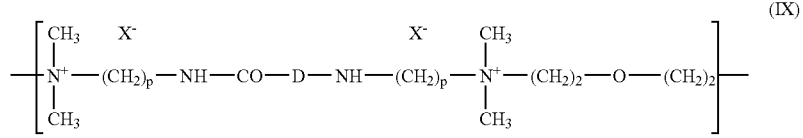

and, for example, those polymers of formula (W) whose molecular weight, determined by gel permeation chromatography, ranges from 9500 to 9900;

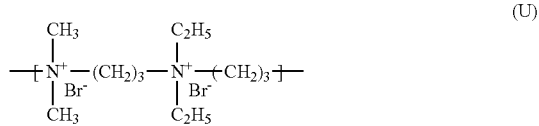

and for example those polymers of formula (U) whose molecular weight, determined by gel permeation chromatography, is 1200.

The amphoteric polymers that may be used in accordance with the present disclosure may be chosen from polymers comprising units K and M randomly distributed in the polymer chain, wherein K is a unit derived from monomers comprising at least one basic nitrogen atom and M is a unit derived from acidic monomers comprising at least one carboxylic or sulfonic group, and alternatively K and M may be chosen from groups derived from zwitterionic carboxybetaine or sulfobetaine monomers; K and M may also be chosen from cationic polymer chains comprising primary, secondary, tertiary or quaternary amine groups, wherein at least one of the amine groups bears a carboxylic or sulfonic group linked via a hydrocarbon-based radical, or alternatively K and M form part of a chain of a polymer comprising an $\alpha,\beta$-dicarboxylic ethylene unit wherein one of the carboxylic groups has been made to react with a polyamine comprising at least one primary or secondary amine group.

The amphoteric polymers corresponding to the above definition that may, for example, be chosen from the following polymers:

(1) polymers resulting from the copolymerization of a monomer derived from a vinyl compound bearing a carboxylic group such as, acrylic acid, methacrylic acid, maleic acid, α-chloroacrylic acid, and from a substituted vinyl compound comprising at least one basic atom, such as, dialkylaminoalkyl methacrylate and acrylate, dialkylaminoalkylmethacrylamide and -acrylamide. Such compounds are described in U.S. Pat. No. 3,836,537. Non-limiting mention may also be made of the sodium acrylate/acrylamidopropyltrimethylammonium chloride copolymer sold under the name Polyquart KE 3033 by the company Henkel.

The vinyl compound may also be a dialkyldiallylammonium salt such as dimethyldiallylammonium chloride. The copolymers of acrylic acid and of the latter monomer are sold under the names MERQUAT 280, MERQUAT 295 and MERQUAT PLUS 3330 by the company Calgon.

(2) Polymers comprising units derived from:
a) at least one monomer chosen from acrylamides and methacrylamides substituted on the nitrogen with an alkyl radical,
b) at least one acidic comonomer comprising at least one reactive carboxylic group, and
c) at least one basic comonomer such as esters comprising primary, secondary, tertiary and quaternary amine substituents of acrylic and methacrylic acids and the product of quaternization of dimethylaminoethyl methacrylate with dimethyl or diethyl sulfate.

In at least one embodiment, the N-substituted acrylamides or methacrylamides are groups wherein the alkyl radicals comprise 2 to 12 carbon atoms, for example, N-ethylacrylamide, N-tert-butylacrylamide, N-tert-octylacrylamide, N-octylacrylamide, N-decylacrylamide, N-dodecylacrylamide and the corresponding methacrylamides.

The acidic comonomers may be chosen, for instance, from acrylic acid, methacrylic acid, crotonic acid, itaconic acid, maleic acid, and fumaric acid and from alkyl monoesters, comprising 1 to 4 carbon atoms, of maleic or fumaric acids or anhydrides.

Non-limiting examples of the basic comonomers are aminoethyl, butylaminoethyl, N,N'-dimethylaminoethyl and N-tert-butylaminoethyl methacrylates.

The copolymers whose CTFA (4th edition, 1991) name is Octylacrylamide/acrylates/butylaminoethyl methacrylate copolymer such as the products sold under the name AMPHOMER or LOVOCRYL 47 by the company National Starch may be used in at least one embodiment.

(3) Polyamino amides that are crosslinked and alkylated partially or totally derived from polyamino amides of general formula:

wherein $R_{19}$ is chosen from divalent radicals derived from a saturated dicarboxylic acid, a mono- or dicarboxylic aliphatic acid comprising an ethylenic double bond, an ester of a lower alkanol, comprising 1 to 6 carbon atoms, of these acids or a radical derived from the addition of any one of the said acids to a bis(primary) or bis(secondary) amine, and Z denotes a bis(primary), mono- or bis(secondary) polyalkylenepolyamine radical and is chosen from:
a) in amounts ranging from 60 to 100 mol %, the radical

wherein x is equal to 2 and p is equal to 2 or 3, or alternatively x is equal to 3 and p is equal to 2,
this radical being derived from diethylenetriamine, from triethylenetetraamine or from dipropylenetriamine;
b) in amounts ranging from 0 to 40 mol %, the radical (XI) above wherein x is equal to 2 and p is equal to 1 and wherein said radical is derived from ethylenediamine, or the radical derived from piperazine:

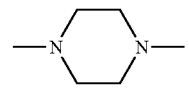

c) in amounts ranging from 0 to 20 mol %, the —NH—(CH$_2$)$_6$—NH— radical derived from hexamethylenediamine, these polyamino amines being crosslinked by addition of a difunctional crosslinking agent chosen from epihalohydrins, diepoxides, dianhydrides and bis-unsaturated derivatives, using from 0.025 to 0.35 mol of crosslinking agent per amine group of the polyamino amide and alkylated by the action of acrylic acid, chloroacetic acid or an alkane sultone, and salts thereof.

The saturated carboxylic acids may be chosen from acids comprising 6 to 10 carbon atoms, such as adipic acid, 2,2,4-trimethyladipic acid and 2,4,4-trimethyladipic acid, terephthalic acid and acids comprising an ethylenic double bond, for instance acrylic acid, methacrylic acid and itaconic acid.

In at least one embodiment, the alkane sultones used in the alkylation may be, for example, propane sultone or butane sultone, and the salts of the alkylating agents may be the sodium or potassium salts.

(4) Polymers comprising zwitterionic units of formula:

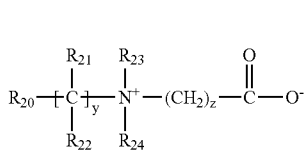
(XII)

wherein $R_{20}$ is chosen from polymerizable unsaturated groups such as acrylates, methacrylates, acrylamides or methacrylamide groups, y and z are chosen from an integer from 1 to 3, $R_{21}$ and $R_{22}$ are chosen from hydrogen atoms, methyl, ethyl and propyl, $R_{23}$ and $R_{24}$ are chosen from hydrogen atoms and alkyl radicals such that the sum of the carbon atoms in $R_{23}$ and $R_{24}$ does not exceed 10.

The polymers comprising such units can also comprise units derived from nonzwitterionic monomers such as dimethyl or diethylaminoethyl acrylate or methacrylate or alkyl acrylates or methacrylates, acrylamides or methacrylamides or vinyl acetate.

By way of example, non-limiting mention may be made of the copolymer of butyl methacrylate/dimethyl carboxymethylammonioethyl methacrylate such as the product sold under the name DIAFORMER Z301 by the company Sandoz.

(5) Chitosan-based polymers comprising monomer units corresponding to formulae (XIII), (XIV) and (XV) below:

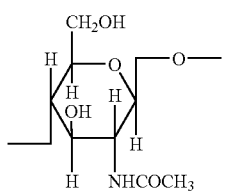
(XIII)

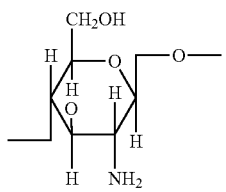
(XIV)

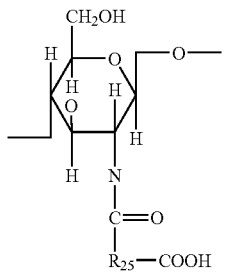
(XV)

the unit (XIII) being present in amounts ranging from 0 to 30%, the unit (XIV) in amounts ranging from 5% to 50% and the unit (XV) in amounts ranging from 30% to 90%, it being understood that, in this unit (XV), $R_{25}$ is chosen from radicals of formula:

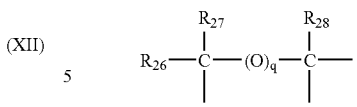

wherein if q is equal to 0, $R_{26}$, $R_{27}$ and $R_{28}$, which may be identical or different, each are chosen from hydrogen atoms, from methyl, hydroxyl, acetoxy and amino residues, from monoalkylamine residues and dialkylamine residues which are optionally interrupted by at least one nitrogen atom and/or optionally substituted with at least one group chosen from amine, hydroxyl, carboxyl, alkylthio and sulfonic groups, and from alkylthio residues in which the alkyl group bears an amino residue, at least one of the radicals $R_{26}$, $R_{27}$ and $R_{28}$ being, in this case, a hydrogen atom;

or, if q is equal to 1, $R_{26}$, $R_{27}$ and $R_{28}$ each are chosen from hydrogen atoms, and also the salts formed by these compounds with bases or acids.

(6) Polymers derived from the N-carboxyalkylation of chitosan, such as N-carboxymethylchitosan or N-carboxybutylchitosan sold under the name "Evalsan" by the company Jan Dekker.

(7) Polymers corresponding to the general formula (XVI) such as those described, for example, in French Patent No. 1 400 366:

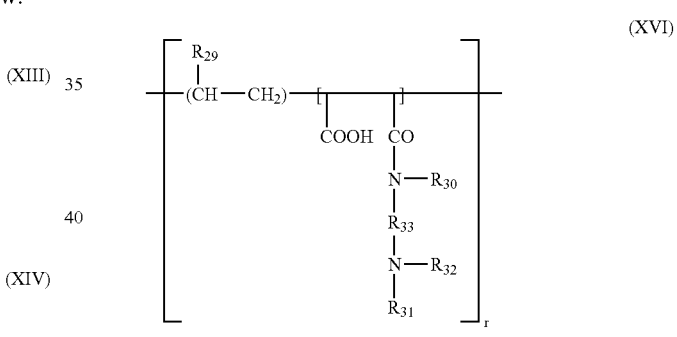
(XVI)

wherein $R_{29}$ is chosen from a hydrogen atom and radicals $CH_3O$, $CH_3CH_2O$ and phenyl, $R_{30}$ is chosen from hydrogen and lower alkyl radicals such as methyl and ethyl, $R_{31}$ is chosen from hydrogen and lower alkyl radicals such as methyl and ethyl, $R_{32}$ is chosen from lower alkyl radicals such as methyl or ethyl and radicals corresponding to the formula: $—R_{33}—N(R_{31})_2$, $R_{33}$ is chosen from $—CH_2—CH_2—$, $—CH_2—CH_2—CH_2—$ and $—CH_2—CH(CH_3)—$ groups, $R_{31}$ having the meanings mentioned above, and r is a number greater than 1, and also the higher homologues of these radicals and comprising up to 6 carbon atoms.

(8) Amphoteric polymers of the type -D-X-D-X- chosen from:

a) polymers obtained by the action of chloroacetic acid or sodium chloroacetate on compounds comprising at least one unit of formula:

-D-X-D-X-D- (XVII)

wherein D is a radical

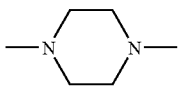

and X is the symbol E or E', E or E', which may be identical or different, is chosen from divalent radicals which are alkylene radicals with a straight or branched chain comprising up to 7 carbon atoms in each main chain, which is unsubstituted or substituted with hydroxyl groups and which can comprise, in addition to the oxygen, nitrogen and sulfur atoms, 1 to 3 aromatic and/or heterocyclic rings; the oxygen, nitrogen and sulfur atoms being present in the form of ether, thioether, sulfoxide, sulfone, sulfonium, alkylamine or alkenylamine groups, hydroxyl, benzylamine, amine oxide, quaternary ammonium, amide, imide, alcohol, ester and/or urethane groups;

b) polymers of formula:

<p align="center">-D-X-D-X-  (XVIII)</p> wherein D is a radical

and X is the symbol E or E' and at least once E'; E having the meaning given above and E' being chosen from divalent radicals which are alkylene radicals with a straight or branched chain having up to 7 carbon atoms in each main chain, which is unsubstituted or substituted with at least one hydroxyl radical and comprising at least one nitrogen atom, the nitrogen atom being substituted with an alkyl chain which is optionally interrupted with an oxygen atom and necessarily comprising at least one carboxyl function or at least one hydroxyl function and betainized by reaction with chloroacetic acid or sodium chloroacetate.

(9) ($C_1$-$C_5$)alkyl vinyl ether/maleic anhydride copolymers partially modified by semi-amidation with an N,N-dialkylaminoalkylamine such as N,N-dimethylaminopropylamine or by semi-esterification with an N,N-dialkanolamine. These copolymers can also comprise other vinyl comonomers such as vinylcaprolactam.

According to one embodiment of the present disclosure, the amphoteric polymers are chosen from those of family (1).

According to the disclosure, the cationic or amphoteric substantive polymer(s), when they are present, are present in an amount ranging from 0.01% to 10% by weight relative to the total weight of the dye composition, for example from 0.05% to 5% by weight, such as from 0.1% to 3% by weight, relative to the total weight of the dye composition.

The medium that is suitable for dyeing keratin fibres generally comprises water or a mixture of water and of at least one organic solvent to dissolve the compounds that are not sufficiently water-soluble. Non-limiting examples of organic solvents that may be mentioned include $C_1$-$C_4$ lower alkanols, such as ethanol and isopropanol; polyols and polyol ethers, for instance 2-butoxyethanol, propylene glycol, propylene glycol monomethyl ether, diethylene glycol monoethyl ether and monomethyl ether, and also aromatic alcohols, for instance benzyl alcohol or phenoxyethanol, and mixtures thereof.

The solvent(s) may be present in the composition in an amount ranging from 1% to 40% by weight relative to the total weight of the dye composition, and for example ranging from 5% to 30% by weight relative to the total weight of the dye composition.

The composition may also comprise additives that are common in the field, such as organic or mineral thickeners; antioxidants; penetrants; sequestrants; fragrances; buffers; dispersants; conditioning agents other than the cationic or amphoteric substantive polymers, for instance cations, or volatile or non-volatile, modified or unmodified silicones; film-forming agents; ceramides; preserving agents; stabilizers; opacifiers.

Needless to say, a person skilled in the art will take care to select this or these optional additional compound(s) such that the advantageous properties intrinsically associated with the composition in accordance with the disclosure are not, or are not substantially, adversely affected by the envisaged addition(s).

As indicated previously, the present disclosure also relates to a process for dyeing keratin materials using the composition according to the disclosure.

According to a first embodiment of the present disclosure, the process comprises applying the composition in the absence of an oxidizing agent, to keratin materials, such as wet or dry fibers, with or without final rinsing of the composition.

In the case of this embodiment, the composition according to the disclosure does not comprise any oxidation dye precursor, but doe contain at least one direct dye.

According to a second embodiment of the disclosure, the process comprises applying the composition according to the disclosure, in the presence of an oxidizing agent, to wet or dry keratin materials, and then leaving it on for a period that is sufficient to obtain the desired coloration.

According to a first possibility, at least one dye composition according to the disclosure and an oxidizing composition are applied to the said keratin fibers simultaneously or successively without intermediate rinsing.

The composition applied is a "ready-to-use composition", i.e. a composition obtained by extemporaneous mixing of at least one dye composition according to the disclosure with a composition comprising at least one oxidizing agent.

In this case, the dye composition may comprise at least one oxidation dye precursor. It may also comprise at least one direct dye, when lightening of the keratin fibers is desired in combination with dyeing.

Obviously, the dye composition may comprise a combination of oxidation dye precursors and of direct dyes.

The oxidizing agent present in the oxidizing composition may be chosen, for example, from hydrogen peroxide, urea peroxide, alkali metal bromates, persalts such as perborates and persulfates, and enzymes such as peroxidases and two-electron or four-electron oxidoreductases. In one embodiment, the oxidizing agent is hydrogen peroxide.

The amount of oxidizing agent in the composition ranges from 1% to 40% by weight relative to the total weight of the ready-to-use composition, and for example may range from 1% to 20% by weight relative to the total weight of the ready-to-use composition.

In at least one embodiment, the oxidizing composition used is an aqueous composition and may be in the form of a solution or an emulsion.

The composition free of oxidizing agent may be mixed with 0.5 to 10 weight equivalents of the oxidizing composition.

It should be noted that the pH of the ready-to-use composition may range from 3 to 12, for example from 4 to 11, such as from 6.5 to 10.5.

The pH of the ready-to-use composition may be adjusted using a basifying or acidifying agent chosen from those mentioned previously.

Still in the case where the composition is applied in the presence of an oxidizing agent, the process may comprise a preliminary step comprising storing, on the one hand, at least one dye composition according to the disclosure and, on the other hand, a composition comprising at least one oxidizing agent in a medium that is suitable for dyeing human keratin fibers, and then in mixing them together at the time of use, before applying this mixture to the wet or dry keratin materials.

Irrespective of the embodiment, i.e. in the presence or absence of oxidizing agent, the time required to develop the coloration ranges from a few seconds to 60 minutes and for example from 1 to 50 minutes.

The temperature required to develop the coloration generally ranges from room temperature (15 to 25° C.) to 250° C., for example ranging from room temperature to 180° C. and further for example from room temperature to 60° C.

Once the time required to develop the coloration has elapsed, the composition may be removed.

This may take place in a conventional manner, either by performing at least one rinsing operation, or by performing at least one washing and rinsing operation, or by performing a combination thereof. Finally, the keratin materials are dried or are left to dry.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements.

The following examples are intended to illustrate the invention in a non-limiting manner.

EXAMPLES

The dye composition below was prepared (amounts expressed in grams):

| EXAMPLE 1 | Composition |
| --- | --- |
| Double-distilled pure cetyl alcohol (Lanette 16; from Cognis) | 10.2 |
| Oxyethylenated (10 OE) oleyl alcohol (Brij 96 V; from Uniqema) | 4 |
| Sodium laurylpolyglucoside (n = 1.4) ether carboxylate at 30% in water (Plantapon LGC Sorb; from Cognis) | 0.8 |
| Glyceryl stearate (Tegin 6070; from Goldschmidt) | 5.8 |

-continued

| EXAMPLE 1 | Composition |
| --- | --- |
| Decyl oleate (Cetiol V; from Cognis) | 1.8 |
| Oleic acid | 2.73 |
| Pure monoethanolamine | 0.52 |
| Ammonium thiolactate as an aqueous 58% solution | 0.8 |
| Ascorbic acid | 0.25 |
| Titanium oxide (untreated anatase) coated with polydimethylsiloxane (98/2) | 0.15 |
| Citric acid | 0.31 |
| Aqueous ammonia (20% ammonia) | 11.1 |
| 1-Hydroxy-4-aminobenzene | 0.545 |
| 1-Methyl-2-hydroxy-4-aminobenzene | 0.615 |
| Fragrance | 0.95 |
| Deionized water | 59.43 |

| EXAMPLE 2 | Composition |
| --- | --- |
| Double-distilled pure cetyl alcohol | 8.50 |
| Oxyethylenated (30 OE) oleyl alcohol | 4.00 |
| Sodium laurylpolyglucoside (n = 1.4) ether carboxylate at 30% in water (Plantapon LGC Sorb; from Cognis) | 0.50 |
| Glyceryl stearate | 5.00 |
| Decyl oleate (Cetiol V; from Cognis) | 1.80 |
| Oleic acid | 2.65 |
| Pure monoethanolamine | 0.50 |
| Ascorbic acid | 0.25 |
| Reticulated polyacrylic acid (Carbomer) | 0.30 |
| EDTA | 0.31 |
| Aqueous ammonia (20% ammonia) | 11.1 |
| 1-Hydroxy-4-aminobenzene | 0.545 |
| 1-Methyl-2-hydroxy-4-aminobenzene | 0.615 |
| Fragrance | 0.95 |
| Deionized water | qsp |

The above dye compositions were mixed, at the time of use, in a plastic bowl and for 2 minutes, with an aqueous oxidizing composition comprising 6% hydrogen peroxide, at a rate of 1 part of dye composition per 1.5 parts of oxidizing composition. The mixing was quick and easy.

The mixture obtained was applied to locks of natural hair comprising 90% white hairs, and was left on for 20 minutes.

The application was quick and easy. The product stayed in place perfectly, did not run, and spread well from the root to the end.

The locks were then rinsed with water, washed with a standard shampoo, rinsed again with water, and then dried and disentangled. The mixture was satisfactorily removed on rinsing.

The hair was dyed in a strong coppery red shade. Furthermore, the hair was not coarse.

What is claimed is:

1. A dye composition comprising, in a medium that is suitable for dyeing keratin fibers:
    at least one dye chosen from oxidation dye precursors and direct dyes;
    at least one alkoxylated and/or glycerolated nonionic surfactant;
    at least one anionic surfactant;
    at least one fatty alcohol;
    at least one non-ethoxylated fatty acid ester of a $C_1$-$C_{10}$ monohydroxylated alcohol;
    wherein the weight ratio of the total amount of fatty alcohols to the total amount of nonionic and anionic surfactants is greater than 0.5; and
    wherein the dye composition comprises at least 55% water relative to the total weight of the dye composition.

2. A dye composition according to claim 1, wherein the dye composition comprises water in an amount of at least 60% by weight relative to the total weight of the dye composition.

3. A dye composition according to claim 1, wherein the at least one nonionic surfactant is chosen from:
oxyalkylenated or glycerolated fatty alcohols;
oxyalkylenated alkylphenols in which the alkyl chain has 8 to 18 carbon atoms;
oxyalkylenated or glycerolated fatty amides;
oxyalkylenated plant oils;
optionally oxyalkylenated fatty acid esters of sorbitan;
optionally oxyalkylenated fatty acid esters of sucrose;
fatty acid esters of polyethylene glycol;
$(C_6-C_{30})$alkylpolyglycosides;
N—$(C_6-C_{30})$alkylglucamine derivatives;
amine oxides;
copolymers of ethylene oxide and of propylene oxide; and
mixtures thereof.

4. A dye composition according to claim 3, wherein said amine oxides are chosen from $(C_{10}-C_{14})$alkylamine oxides and N-acylaminopropylmorpholine oxides.

5. A dye composition according to claim 1 wherein the at least one nonionic surfactant is chosen from oxyalkylenated and glycerolated fatty alcohols.

6. A dye composition according to claim 1, wherein the at least one nonionic surfactant is present in an amount ranging from 0.01% to 50% by weight relative to the total weight of the dye composition.

7. A dye composition according to claim 1, wherein the at least one anionic surfactant is chosen from:
$(C_6-C_{30})$alkyl sulfates, $(C_6-C_{30})$alkyl ether sulfates, $(C_6-C_{30})$alkylamido ether sulfates, alkylaryl polyether sulfates, monoglyceride sulfates;
$(C_6-C_{30})$alkylsulfonates, $(C_6-C_{30})$alkylamide sulfonates, $(C_6-C_{30})$alkylaryl sulfonates, α-olefin sulfonates, paraffin sulfonates;
$(C_6-C_{30})$alkyl phosphates;
$(C_6-C_{30})$alkyl sulfosuccinates, $(C_6-C_{30})$alkyl ether sulfosuccinates, $(C_6-C_{30})$alkylamide sulfosuccinates;
$(C_6-C_{30})$alkyl sulfoacetates;
$(C_6-C_{24})$acyl sarcosinates;
$(C_6-C_{24})$acyl glutamates;
$(C_6-C_{30})$alkylpolyglycoside carboxylic ethers; $(C_6-C_{30})$ alkylpolyglycoside sulfosuccinates;
$(C_6-C_{30})$alkyl sulfosuccinamates;
$(C_6-C_{24})$acyl isethionates;
N—$(C_6-C_{24})$acyl taurates;
fatty acid salts;
$(C_8-C_{20})$acyl lactylates;
$(C_6-C_{30})$alkyl-D-galactoside uronic acid salts;
polyoxyalkylenated$(C_6-C_{30})$alkyl ether carboxylic acid salts, polyoxyalkylenated$(C_6-C_{30})$alkylaryl ether carboxylic acid salts, polyoxyalkylenated$(C_6-C_{30})$alkylamido ether carboxylic acid salts;
and mixtures thereof.

8. A dye composition according to claim 1, wherein the at least one anionic surfactant is present in an amount ranging from 0.01% to 50% by weight relative to the total weight of the dye composition.

9. A dye composition according to claim 1, wherein the at least one fatty alcohol is present in an amount ranging from 0.1% to 30% by weight relative to the total weight of the dye composition.

10. A dye composition according to claim 1, wherein the weight ratio of the total amount of fatty alcohols to the total amount of nonionic and anionic surfactants is greater than 0.75.

11. A dye composition according to claim 1, wherein the composition comprises at least one fatty substance other than the at least one fatty alcohol.

12. A dye composition according to claim 11, wherein the at least one fatty substance is chosen from non-oxyalkylenated, non-glycerolated fatty acid amides, carboxylic acid monoesters and polyesters, mineral oils and plant oils, and mixtures thereof.

13. A dye composition according to claim 1, wherein the at least one non-ethoxylated fatty acid ester of a $C_1-C_{10}$ alcohol is a monoester, diester or triester of a linear or branched, saturated or unsaturated $C_8-C_{30}$ carboxylic acid and of a linear or branched, saturated or unsaturated $C_1-C_{10}$ monohydroxylated alcohol, with the exception of monoethylene and diethylene.

14. A dye composition according to claim 13, wherein the at least one fatty acid ester is chosen from the monoesters, diesters or triesters of oleic acid, lauric acid, palmitic acid, myristic acid, behenic acid, stearic acid, linoleic acid, linolenic acid, capric acid or arachidonic acid, and of methanol, ethanol, propanol, isopropanol, octanol or decanol, and also mixtures thereof.

15. A dye composition according to claim 1, wherein the at least one non-ethoxylated fatty acid ester of a $C_1-C_{10}$ alcohol is present in an amount ranging from 0.1% to 20% by weight relative to the total weight of the dye composition.

16. A dye composition according to claim 1, wherein the at least one oxidation dye precursor is chosen from oxidation bases and couplers, and mixtures thereof.

17. A dye composition according to claim 16, wherein the composition comprises oxidation base(s) in an amount ranging from 0.0005% to 12% by weight relative to the total weight of the dye composition.

18. A dye composition according to claim 16, wherein the composition comprises coupler(s) in an amount ranging from 0.0001% to 15% by weight relative to the total weight of the dye composition.

19. A dye composition according to claim 1, wherein the at least one direct dye is present in an amount ranging from 0.0005% to 15% by weight relative to the total weight of the dye composition.

20. A dye composition according to claim 1, wherein the composition further comprises at least one basifying agent.

21. A dye composition according to claim 20, wherein the at least one basifying agent is chosen from aqueous ammonia, alkanolamines and combinations of $C_2-C_{10}$ alkanolamines with alkali metal or alkaline-earth metal silicates.

22. A dye composition according to claim 1, further comprising at least one cationic or amphoteric substantive polymer.

23. A dye composition according to claim 22, wherein the at least one cationic or amphoteric substantive polymer is present in an amount ranging from 0.01% to 10% by weight relative to the total weight of the dye composition.

24. A dye composition according to claim 1, further comprising at least one oxidizing agent.

25. A process for dyeing keratin fibers comprising
applying to wet or dry keratin fibers a dye composition comprising, in a medium that is suitable for dyeing keratin fibers:
at least one dye chosen from oxidation dye precursors and direct dyes;
at least one alkoxylated and/or glycerolated nonionic surfactant;
at least one anionic surfactant;
at least one fatty alcohol;

at least one non-ethoxylated fatty acid ester of a $C_1$-$C_{10}$ monohydroxylated alcohol;

wherein the weight ratio of the total amount of fatty alcohols to the total amount of nonionic and anionic surfactants is greater than 0.5; and wherein the dye composition comprises at least 55% water relative to the total weight of the dye composition.

26. A process for dyeing keratin fibers comprising applying to wet or dry keratin fibers a dye composition, in the presence of at least one oxidizing composition, wherein said at least one oxidizing composition is applied simultaneously with or successively to the dye composition without intermediate rinsing, leaving the mixture on the fibers, and rinsing the fibers, wherein the dye composition comprises, in a medium that is suitable for dyeing keratin fibers:
- at least one dye chosen from oxidation dye precursors and direct dyes;
- at least one alkoxylated and/or glycerolated nonionic surfactant;
- at least one anionic surfactant;
- at least one fatty alcohol;
- at least one non-ethoxylated fatty acid ester of a $C_1$-$C_{10}$ monohydroxylated alcohol;

wherein the weight ratio of the total amount of fatty alcohols to the total amount of nonionic and anionic surfactants is greater than 0.5; and wherein the dye composition comprises at least 55% water relative to the total weight of the dye composition.

27. A process for dyeing keratin fibers, comprising applying to wet or dry keratin fibers, in the presence of at least one oxidizing composition, a dye composition, wherein said at least one oxidizing composition is mixed with the dye composition before application, wherein said dye composition comprises, in a medium that is suitable for dyeing keratin fibers:
- at least one dye chosen from oxidation dye precursors and direct dyes;
- at least one alkoxylated and/or glycerolated nonionic surfactant;
- at least one anionic surfactant;
- at least one fatty alcohol;
- at least one non-ethoxylated fatty acid ester of a $C_1$-$C_{10}$ monohydroxylated alcohol;

wherein the weight ratio of the total amount of fatty alcohols to the total amount of nonionic and anionic surfactants is greater than 0.5; and wherein the dye composition comprises at least 55% water relative to the total weight of the dye composition.

28. A multi-compartment device for dyeing keratin fibers comprising a first compartment comprising a dye composition comprising, in a medium that is suitable for dyeing keratin fibers:
- at least one dye chosen from oxidation dye precursors and direct dyes;
- at least one alkoxylated and/or glycerolated nonionic surfactant;
- at least one anionic surfactant;
- at least one fatty alcohol;
- at least one non-ethoxylated fatty acid ester of a $C_1$-$C_{10}$ monohydroxylated alcohol;

wherein the weight ratio of the total amount of fatty alcohols to the total amount of nonionic and anionic surfactants is greater than 0.5; and wherein the dye composition comprises at least 55% water relative to the total weight of the dye composition, and comprising a second compartment comprising an oxidizing composition.

* * * * *

UNITED STATES PATENT AND TRADEMARK OFFICE
CERTIFICATE OF CORRECTION

PATENT NO. : 7,651,533 B2  Page 1 of 1
APPLICATION NO. : 11/393694
DATED : January 26, 2010
INVENTOR(S) : Frédéric Legrand It is certified that error appears in the above-identified patent and that said Letters Patent is hereby corrected as shown below:

Title page, column 1, delete
Item "(76) Inventor:   Frédéric Legrand, 2-1-4,
                     Ichigayasadoharacho, Crest court
                     Sadohara #313, Shinjuku-ku, 162-0842
                     Tokyo (JP)"
and insert on the Title page therefor:
Item --(75) Inventor:   Frédéric Legrand, Tokyo (JP)

Item  (73) Assignee:   L'Oréal S.A., Paris (FR)--.

Title page, column 2, below "*Primary Examiner*—Elisa B Elhilo", insert
Item --(74) *Attorney, Agent, or Firm*—Finnegan, Henderson, Farabow, Garrett & Dunner, L.L.P.--.

Signed and Sealed this
Twenty-ninth Day of March, 2011

David J. Kappos
*Director of the United States Patent and Trademark Office*